United States Patent [19]
Riley

[11] 4,155,975
[45] May 22, 1979

[54] DEODORANT AND METHOD FOR DEODORIZING LIVESTOCK MANURE

[76] Inventor: Harvey W. Riley, R.F.D. #1 (Box 91), Milford, Nebr. 68405

[21] Appl. No.: 855,421

[22] Filed: Nov. 28, 1977

Related U.S. Application Data

[63] Continuation-in-part of Ser. No. 737,487, Nov. 1, 1976, abandoned.

[51] Int. Cl.² ............... A61L 11/00; A61L 13/00; C02C 1/40
[52] U.S. Cl. .......................... 422/5; 210/62; 210/64; 424/76
[58] Field of Search ............. 21/55, 58; 210/62, 64; 424/76; 422/5

[56] References Cited

U.S. PATENT DOCUMENTS

| | | | |
|---|---|---|---|
| 2,987,435 | 6/1961 | Davies et al. | 21/58 |
| 3,107,216 | 10/1963 | Hamilton | 210/60 |
| 3,288,708 | 11/1966 | Cordle et al. | 210/62 |
| 3,408,295 | 10/1968 | Vaichulis | 210/62 |
| 3,457,167 | 7/1969 | Spiegel et al. | 210/62 |
| 3,649,493 | 3/1972 | Meiners et al. | 210/62 |
| 3,681,492 | 8/1972 | Kotzbauer | 210/64 |
| 3,706,663 | 12/1972 | Peterson | 210/64 |
| 3,884,804 | 5/1975 | Robinson et al. | 210/64 |
| 4,007,262 | 2/1977 | Bowers | 424/76 |
| 4,043,911 | 8/1977 | Melnick et al. | 210/64 |
| 4,108,771 | 8/1978 | Weiss | 422/5 |

Primary Examiner—Morris O. Wolk
Assistant Examiner—Bradley Garris
Attorney, Agent, or Firm—George R. Nimmer

[57] ABSTRACT

Anaerobic livestock manure, comprising an admixture of feces and urine, is deodorized by topically applying onto the manure an aqueous deodorizing-mixture of a suitable iodine ingredient and an oxidizing agent. Preferably, the aqueous deodorizing-mixture comprises elemental iodine, potassium iodide, and alkaline hypochlorite oxidizing agent which has a long term shelf life. For urine-deficient manure piles, wherein urine has been pumped or otherwise removed from the manure feces, the deodorizing-mixture product desirably further contains non-urinary ammoniacal material, such as ammonium nitrate.

5 Claims, No Drawings

DEODORANT AND METHOD FOR DEODORIZING LIVESTOCK MANURE

This is a continuation-in-part of co-pending patent application Ser. No. 737,487, filed Nov. 1, 1976, now abandoned and also entitled "Deodorant And Method For Deodorizing Livestock Manure".

Anaerobic livestock manure, comprising an admixture of animal feces and urine, is offensively odoriferous to livestock tenders and to passersby and to other persons in the geographic vicinity. There has been the continual quest in the prior art to deodorize livestock manure, but which has been of only limited success. For example, it is known that the topical application of various chemicals an microorganisms will deodorize livestock manures, but only for relatively short periods of time. Thus, long term deodorization requires repeated and hence expensive re-applications of the deodorant onto the manure.

It is accordingly the general objective of the present invention to provide a deodorant and method for deodorizing livestock manure which is unusually effective in reducing the offensive odor and for long term durations, which is economically feasible, and which is amenable to long term shelf-life warehousing prior to application for deodorizing livestock manure.

With the above and other objects and advantages in view, which will become more apparent as this description proceeds, the deodorant and method for deodorizing livestock manure of the present invention generally comprises the steps of: making an aqueous deodorizing-mixture comprising an iodous-compound and an oxidizing agent therefor; and topically applying the deodorizing-mixture substantially evenly over the livestock manure to thereby deodorize same for a long term duration. Preferably, the iodous-compound comprises elemental iodine crystals dissolved in water as an iodous-solution, and the oxidizing agent comprises an alkaline hypochlorite in stoichiometric excess. For long term shelf-life and deodorizing effectiveness consistent with economy, elemental iodine, potassium iodide, and calcium hypochlorite are made into an aqueous deodorizing-mixture. For urine-deficient manure piles, wherein the livestock tenders had removed a significant proportion of the urine from the feces, the deodorizing-mixture further contains non-urinary ammoniacal material such as ammonium nitrate. The exact biochemical mechanism for the long term duration and economical effectiveness for the deodorizing-mixture of the present invention is not understood in theory. However, there is some apparently synergistic effect on the livestock manure afforded by the iodous-ingredient in combination with the alkaline hypochlorite or other oxidizing agent, especially when there is also present sufficient ammonia.

EXAMPLE I 10 grams of ethylene diamine dihydroiodide (EDDI) is dissolved in 10 grams water to provide an iodous-solution. 60 grams of calcium hypochlorite is uniformly dispersed into 940 grams water to provide an aqueous solution of oxidizing agent, into which is thereafter dissolved the said 20 grams of iodous-solution. The distinct odor of chlorine gas emanates from this 1,020 grams deodorizing-mixture. Promptly thereafter, and in less than one-half hour, the freshly made 1,020 grams deodorizing-mixture is topically applied by pouring evenly over about 150 pounds of offensively odoriferous hog manure in its naturally deposited state i.e., normal excreta combination gravimetrically or urine and feces. Practically immediately, the foul manure odor is drastically reduced to a tolerable level for a long term duration exceeding seven days, from the single topical application of the 1,020 grams deodorizing-mixture.

EXAMPLE II 2 grams of elemental iodine crystals is dissolved in 50 grams of methanol and then further diluted with 50 grams water to provide 102 grams iodous-solution. 200 grams of hydrated sodium hypochlorite crystals is dissolved in 1,800 grams of water, into which is thereafter dissolved the 102 grams iodous-solution. The distinct odor of chlorine gas emanates from this 2,102 grams deodorizing-mixture. Promptly thereafter, and in less than one-half hour, the freshly made 2,102 grams of deodorizing-mixture is topically applied by pouring evenly over about 300 pounds of offensively odoriferous hog manure in its normally excreted gravimetric ratio of urine and feces. Practically immediately, the foul manure odor is drastically reduced to a tolerably acceptable level for a long term duration exceeding seven days, from said single topical application.

EXAMPLE III 45 grams of elemental iodine crystals and 45 grams of potassium iodide are dissolved in 1,000 grams water to provide 1,090 grams of iodous-solution having a very dark color. 4,500 grams calcium hypochlorite are dissolved in 15,000 grams water to provide 19,500 grams of an aqueous oxidizing agent solution. These two separate solutions (20,590 grams total weight) are mixed into about 55 gallons water as a diluent to provide 60+ gallons of a deodorizing-mixture. This deodorizing-mixture has become of a smoky white color and has a long term shelf-life exceeding several days.

A manure pit measuring 35 feet long by 10 feet wide by 6 feet deep is encountered by the operator and which pit is filled with hog manure in its normally excreted gravimetric ratio of urine and feces. The aforeprovided 60+ gallons deodorizing-mixture is topically applied by pouring over the said encountered pit of hog manure. Within fifteen minutes, the foul manure odor is drastically reduced to a tolerably acceptable level for a long term duration exceeding seven days, from said single topical application.

EXAMPLE IV

A manure pit measuring 35 feet long by 10 feet wide by 6 feet deep is encountered by the operator and which pit is filled with hog manure in its normally excreted gravimetric ratio of urine and feces. The operator pumps away the major proportion of the urine from the manure pit to leve a urine-deficient manure pile within the pit. The said purposely withdrawn urine has utility remote of the pit, such as for agricultural fertilization. The 60+ gallons deodorizing-mixture made according to the procedure of Example III is topically applied by pouring over the said urine-deficient manure pile. However, the foul manure odor remains practically unabated. It is thus apparent that the deodorizing-mixture made in accordance with Example III has only limited utility in suppressing the foul odor of urine-deficient hog manure.

EXAMPLE V

A manure pit measuring 35 feet long by 10 feet wide by 6 feet deep is encountered by the operator and which pit is filled with hog manure in its normally excreted gravimetric ratio of urine and feces. The operator pumps away the major proportion of the urine from the manure pit to leave a urine-deficient manure pile within the pit. The said purposely withdrawn urine has utility as liquid fertilizer at locations remote of the pit, and by so removing the urine periodically the pit can accept greater quantities of manure deposit from the hogs.

The 60+ gallons deodorizing-mixture made according to Example III, except further enriched with non-urinary ammoniacal material, will adequately deodorize the urine-deficient manure pile. Specifically, 45 grams of elemental iodine crystals and 45 grams of potassium iodide are dissolved in 1,000 grams water to provide 1,090 grams of iodous-solution having a very dark color. 4,500 grams calcium hypochlorite and 450 grams ammonium nitrate, artificially synthesized as a chemical reaction between ammonia and nitric acid, are dissolved into 20,000 grams water to provide 24,950 grams of an aqueous oxiding agent solution enriched with non-urinary ammoniacal material. These two separate solutions (26,040 grams total weight) are mixed into about 55 gallons water as a diluent to provide 60+ gallons of deodorizing-mixture. This deodorizing-mixture has become of a cloudy greenish white color and has a long term shelf-life exceeding several days. The said 60+ gallons ammoniacally enriched mixture is topically applied by pouring over the said urine-deficient manure pile. Within fifteen minutes, the foul manure odor is drastically reduced to a tolerably acceptable level for a long term duration exceeding seven days i.e. from said single topical application.

From the foregoing, the deodorant and method for deodorizing livestock manure will be readily understood and further explanation is believed to be unnecessary. However, since numerous modifications and changes will readily occur to those skilled in the art, it is not desired to limit the invention to the exact modes and examples described, and accordingly, all suitable modifications and equivalents may be resorted to, falling within the scope of the appended claims.

I claim:

1. Method for deodorizing livestock manure consisting of urine-deficient feces, said method comprising the following steps:
   A. making a deodorizing-mixture comprising in aqueous medium an iodous-ingredient including therein elemental iodine and potassium iodide, alkaline hypochlorite oxidizing agent for said iodous-ingredient, and ammonium nitrate; and
   B. topically applying the said deodorizing-mixture substantially evenly over the livestock manure to deodorize same.

2. The method of claim 1 wherein making the deodorizing-mixture comprises the steps of:
   (i) dissolving about 45 parts by weight each of elemental iodine and potassium iodide into at least 1,000 parts by weight water to provide an iodous-solution, and
   (ii) dissolving about 4,500 parts by weight calcium hypochlorite as said alkaline hypochlorite and about 450 parts by weight ammonium nitrate into at least 15,000 parts by weight water.

3. A deodorizing-mixture for deodorizing livestock manure consisting of urine-deficient feces, said deodorizing-mixture comprising an aqueous mixture of iodous-ingredient including therein elemental iodine and potassium iodide, an oxidizing agent for said iodous-ingredient, and ammonium nitrate.

4. The deodorizing-mixture of claim 3 wherein calcium hypochlorite comprises said oxidizing agent.

5. The aqueous deodorizing-mixture of claim 4 comprising about 45 parts by weight each of elemental iodine and potassium iodide, about 4,500 parts by weight calcium hypochlorite, and at least about 16,000 parts by weight water.

* * * * *